United States Patent
Muir et al.

(10) Patent No.: US 10,947,204 B1
(45) Date of Patent: Mar. 16, 2021

(54) METHOD FOR PREPARING SODIUM NITROTETRAZOLATE USING CATION EXCHANGE RESIN

(71) Applicant: U.S. Government as Represented by the Secretary of the Army, Dover, NJ (US)

(72) Inventors: R. Hunter Muir, Middletown, CT (US); Andrew G. Pearsall, East Lyme, CT (US); Jerry S. Salan, East Lyme, CT (US); Matthew L. Jorgensen, East Lyme, CT (US); Jon G. Bragg, Essex, CT (US); Neha Mehta, Succasunna, NJ (US); John W. Fronabarger, Sun Lakes, AZ (US); Jason B. Pattison, Phoenix, AZ (US); Lily F. W. Walsh, Phoenix, AZ (US)

(73) Assignee: U.S. Government as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 16/655,636

(22) Filed: Oct. 17, 2019

(51) Int. Cl.
*C07D 257/06* (2006.01)
*B01J 39/05* (2017.01)

(52) U.S. Cl.
CPC ............ *C07D 257/06* (2013.01); *B01J 39/05* (2017.01)

(58) Field of Classification Search
CPC ................................ C07D 257/06; B01J 39/05
See application file for complete search history.

(56) References Cited

U.S. PATENT DOCUMENTS

| | | | |
|---|---|---|---|
| 4,093,623 A | 6/1978 | Gilligan | |
| 9,598,380 B2 * | 3/2017 | Bottaro | ................ C07D 257/06 |
| 9,670,168 B2 * | 6/2017 | Bragg | .................. C07D 257/06 |
| 9,718,791 B2 | 8/2017 | Bragg | |

* cited by examiner

*Primary Examiner* — Karen Cheng
(74) *Attorney, Agent, or Firm* — John P. DiScala

(57) ABSTRACT

The present invention is directed to a method for preparing 5-nitrotetrazolate using a strongly acidic ionic cation exchange resin that has improve yields over prior art methods. The methods disclosed herein can be used either in a batch process or continuous flow reactor. In one exemplary process, starting material sodium 5-aminotetrazolate in solution is added into a reaction vessel containing a strongly acidic ionic cation exchange resin to facilitate production of 5-nitrotetrazolate. Multiple reactors containing resins may be connected in series to improve 5-nitrotetrazolate yields and purity levels.

16 Claims, 2 Drawing Sheets

METHOD FOR PREPARING SODIUM NITROTETRAZOLATE USING CATION EXCHANGE RESIN

RIGHTS OF THE GOVERNMENT

The inventions described herein may be manufactured and used by or for the United States Government for government purposes without payment of any royalties.

FIELD OF INVENTION

The present invention is directed generally to synthesis of sodium nitrotetrazolate and more specifically to synthesis of sodium nitrotetrazolate using a cation exchange resin.

BACKGROUND OF THE INVENTION

Sodium 5-nitrotetrazolate (NaNT) is a precursor material to copper (1) nitrotetrazolate (DBX-1). Prior art methods of producing NaNT from 5AT is generally performed using the method illustrated in FIG. 1. The starting material, 5-aminotetrazole, or its sodium salt (Na5AT), is reacted with nitrous acid (HONO) in aqueous solution to form 5-diazonium-1H-tetrazole (DHT), a reactive intermediate. DHT reacts with sodium nitrite in aqueous solution to form NaNT and one molar equivalent of nitrogen gas.

U.S. Pat. No. 9,718,791 to Bragg et al, describe a method for generating NaNT in a tubular style reactor suitable for production of teraamine-cis-bis(5-nitro-2H-tetrazolato-N cobalt(III) perchlorate (BNCP). However, the NaNT produced under this method also generates gas in confined tubes which can be dangerous. In addition, undesirable quantities of tetrazole impurities such as bi-tetrazole-amine and 1H-tetrazole are also produced. The 1H-tetrazole must be removed prior to synthesis of DBX-1 and as such it is desirable to minimize its formation to increase the DBX-1 yield.

U.S. Pat. No. 4,093,623 previously describes preparation of NaNT using batch production methods. This method is undesirable as it requires isolation of the solid acid copper salt of 5-nitrotetrazole—a dangerous solid primary energetic material.

Thus, a need exists for a safe and efficient method to produce NaNT without isolating solid explosives in the process or generating high levels of impurities. The methods disclosed herein improves upon current methods by disclosing a continuous process for generating NaNT at higher purity levels.

SUMMARY OF THE INVENTION

The object of the present invention to provide methods for preparing 5-nitrotetrazolate and its sodium salt by introducing a solution of 5-aminotetrazole (5-AT) into reactor wherein said reactor comprises sodium nitrite solution at pH between 3 and 7 and a strong acidic cation exchange resin to produce a first reaction solution comprising 5-nitrotetrazolate.

It is a further object of the invention to transfer the first reaction solution comprising 5-nitrotetrazolate from a first reactor to a second reactor comprising a strong acidic cation exchange resin to form another reaction solution comprising 5-nitrotetrazolate content that is greater than the 5-nitrotetrazolate in the first reaction solution and to transfer the reaction solution to a purification reactor to remove impurities in the transfer reaction.

In another object of the invention, the reactor may be a batch or continuous flow reactor or continuous stir tank reactor.

BRIEF DESCRIPTION OF THE DRAWINGS

Further features and advantages of the present invention may be understood from the drawings.

DETAILED DESCRIPTION

The invention disclosed herein is directed to a method for preparing 5-nitrotetrazolate and its sodium salt. The process utilizes a solution of 5-aminotetrazole (5AT) mixed with aqueous solutions of sodium nitrite at pH between 3 and 7 in the presence of a strongly acidic cation exchange resin. The reaction to generate NaNT may be performed in a batch reactor or a continuous flow reactor.

Schematic 1 is a representation of the reaction mechanism for the present invention.

Schematic 1

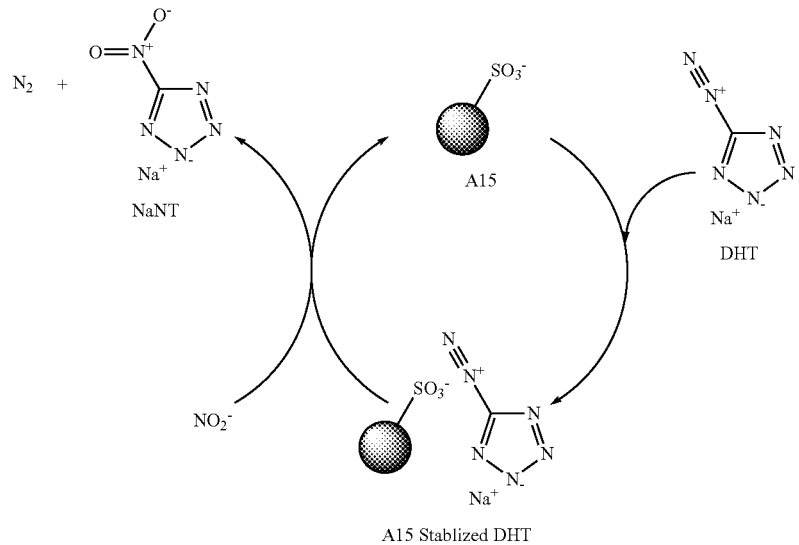

A15 Stablized DHT

The ion exchange resins (e.g. A15) provided herein gives an advantage over prior art syntheses methods by stabilizing the DHT (5-diazonium-1H-tetrazole, a reactive intermediate) as a salt thereby increasing NaNT yield. The proposed mechanism is as follows: The ion exchange resin (A15) forms a salt with DHT, which is labeled as the A15 stabilized DHT. This stabilized salt reacts with nitrite ion in aqueous solution to form NaNT, releasing the A15 sulfonic acid site to stabilize another DHT molecule.

Figure 1:
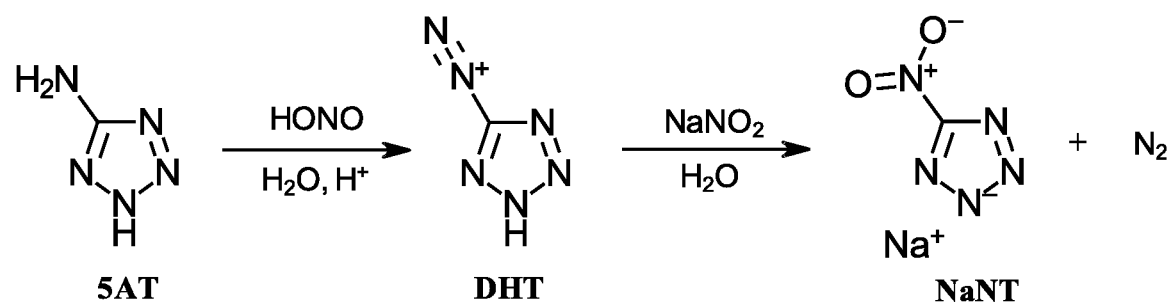
FIG. 1 is a schematic representation of the prior art reaction mechanism for synthesis of NaNT from 5AT.
Figure 2:
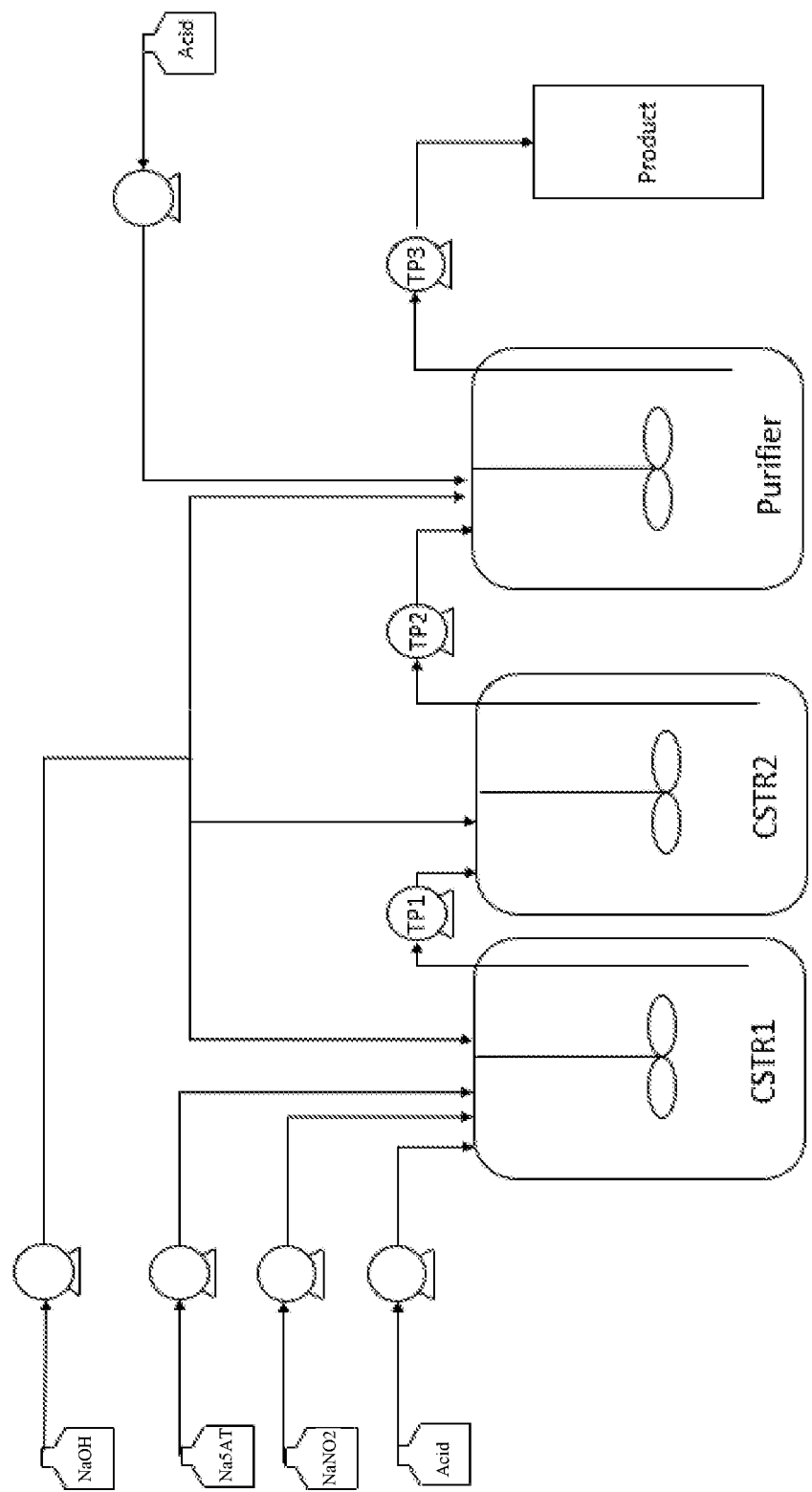
FIG. 2 illustrates an exemplary setup for a continuous stirred tank reactor of the present invention.

FIG. 2 illustrates an exemplary setup for the conversion of 5AT to NaNT using Continuous Stirred Tank Reactors (CSTRs) arranged in a series. This allows for continuous purification of the reaction mixture to remove excess nitrite. It is initiated with an aqueous solution of sodium salt of 5-aminotetrazole (Na5AT), aqueous sodium nitrite (NaNO2) and an aqueous mineral acid solution being added continuously via pumps to CSTR1 (containing a cationic exchange resin), where the reaction to form NaNT occurs. A transfer pump (TP1) may be used to transfer product solution to CSTR2, where the solution is allowed to age to increase the NaNT reaction yield. Reaction mixture may be continuously transferred to a purifier via transfer pump 2 (TP2), where it is combined with an acid, either a cationic exchange resin or mineral acid to remove nitrite ion impurities. Exemplary acids may be nitric acid, sulfuric acid, hydrochloric acid or perchloric acid. Use of a transfer pump (TP3) may be employed to collect product solutions continuously. A sodium hydroxide (NaOH) quench pump was installed with outlets to all reactors to quench the reaction in case of runaway.

The exemplary reaction discussed above may also be accomplish using a fixed bed reactor, tubular slurry reactor, or fluidized bed reactor. Alternatively, the reaction may also occur in a mixing zone such as a cation exchange resin packed column, tubing or stirred tank reactor. The temperature of the reaction may range from 0° C. to 100° C., with 10° C. to 30° C. being preferable.

An acidic resin or cationic exchange resin may be used as an acid source for the reaction to induce the formation of the intermediate species to nitrotetrazolate, the tetrazole diazonium ion (DHT). Use of porous cationic exchange resins, including but not limited to Amberlyst 15 (available from Dow Chemical) or Dowex Marathon C (available from Dow Chemical), may be introduced as a source of protons for the diazotization reaction, and/or to promote increase product purity. This increase in product purity is afforded through two mechanisms. The first of these mechanisms is the selective binding of impurities to the porous resin backbone. The second mechanism is the establishment of low pH region within the resin pores, which promotes the diazotization of 5-aminotetrazole. Meanwhile, the pH of the bulk solution is kept at a desired pH, minimizing formation of impurities such as 1H-tetrazole. This allows for production of higher relative purity raw material than previously described methods to generate copper-free sodium nitrotetrazolate solutions, where the relative purity may be defined as the mass ratio of the nitrotetrazolate to 1H-tetrazole.

The formation and reaction of a metal salt of 5-aminotetrazole through mixing of an aqueous 5AT solution with one molar equivalent of suitable base, which may include but is not limited to potassium hydroxide or sodium hydroxide, may be performed to improve solubility of the starting material in aqueous solution to generate more concentrated NaNT product solutions.

The pH of the reaction may range between 3 and 7, controlled through the dose of a suitable acid such as a mineral or organic acid which can be added to the reaction mixture during addition of 5AT or 5AT salt solutions.

Modifications of certain parameters may help to optimize the reaction and increase product purity. For instance, use of a three to fifty-fold excess (6 to 100 molar equivalents) of a suitable nitrite salt may be added to prevent/reduce impurity formation. In addition, the use of a cationic exchange resin with oxygen or air sparge or bubbler to remove nitrite from product solutions may also increase the purity yield. Further, the generation and reaction of a low metal nitrous acid solution via mixing with a cation exchange resin may also improve product purity.

A diptube and pump to continuously withdraw reaction mixture from a reaction vessel may be used to move the reaction solution from the vessel while keeping the cation exchange particles from leaving the vessel. The diptube may be sheathed with a mesh filter to prevent cation exchange resin particles from entering the pump.

Example 1

A 31.7 mass percent solution of sodium 5-aminotetrazolate was generated by adding 20.0 g solid 5-AT to an aqueous solution containing 1 molar equivalent of sodium hydroxide. 10.0 g of this solution was dosed to a 115 mL stirred tank reactor containing 34.8 g of a 35 mass percent aqueous sodium nitrite solution and 6.0 g of a strongly acidic cation exchange resin (Amberlyst 15). The dose of Na5AT solution was performed over 30 minutes, mixing the vessel at 500 RPM with a glass pitched-blade agitator. The reactor contents were filtered over Watman #2 filter paper after completion of the dose. The resulting solution was added back to the stirred tank reactor and concentrated hydrochloric acid was added slowly to the reactor over 30 minutes until the pH of the solution dropped below 1.0 and the reaction mixture stopped effervescing. The reactor contents were filtered over Whatman Sharkskin filter paper. Aqueous sodium hydroxide was added until the pH of the solution reached 6.5. The resulting NaNT solution had a composition as described in Table 1 as determined by HPLC.

TABLE 1

| NaNT Solution Composition - HPLC | | |
|---|---|---|
| Nitrotetrazole (wt %) | 1H Tetrazole (ppm) | Nitrite Ion (PPM) |
| 5.624 | 1180 | <200 |

Example 2

A 31.7 mass percent solution of sodium 5-aminottrazolate was generated by adding 20.0 g solid 5-AT to an aqueous solution containing 1 molar equivalent of sodium hydroxide. 19.16 g of this solution was dosed to a 115 mL stirred tank reactor containing 66.5 g of a 35 mass percent aqueous sodium nitrite solution and 23.9 g of a strongly acidic cation exchange resin (Amberlyst 15 Wet). The dose of Na5AT solution was performed over 2.5 hours, mixing the vessel at 500 RPM with a glass pitched-blade agitator. A 31.7 mass percent solution of sodium 5-aminotetrazolate was pumped to the reactor concurrently with a 35 mass percent solution of sodium nitrite at rates of 0.16 g/min and 0.56 g/min respectively. A 31 mass percent nitric acid was dosed to the reactor intermittently to keep the pH of the reaction mixture acidic. The resulting product solution was added to a stirred tank reactor and 0.7 g of strongly acidic cation exchange resin per gram of NaNT solution was added slowly to the reactor over 30 minutes until the pH of the solution dropped below 2.0 and the reaction mixture stopped effervescing. The reactor contents were filtered over Whatman Sharkskin filter paper and the filtrate recharged to the reactor. Aqueous sodium hydroxide was added until the pH of the solution rached 6.5. A copper modified iminodiacetic acid resin was formulated by mixing 100 mL of Supelco Diaion CR11 resin with 500 mL of 1M copper chloride solution at ambient temperature for 5 minutes. The resulting solids were filtered over Whatman #2 paper and washed with deionized water until the washes were colorless. A 5 volume percent of copper modified resin was added to the pH adjusted NaNT solution and stirred at ambient temperature for 30 minutes. The resulting slurry was filtered over Whatman #2 and the liquors recharged to the stirred tank vessel. Again, 5 volume percent of copper modified resin was added to the reactor and the contents stirred at ambient temperature for 30 minutes. The resulting slurry was filtered over Whatman #2. The resulting NaNT solution had a composition as described in Table 2 as determined by 1PLC. The mixture was used successfully to generate high purity copper (I) 5-niterazolate.

TABLE 2

| NaNT Solution Composition - HPLC | | |
|---|---|---|
| Nitrotetrazole (wt %) | 1H Tetrazole (ppm) | Nitrite Ion (PPM) |
| 3.8 | ND | <200 |

Example 3

A 25 mL of Dowex Marathon C H+ form cation exchange resin was placed in beaker at ambient temperature with magnetic stir bar. 25 mL raw NaNT solution was added to the beaker and the mixture stirred at 300 RPM. Air was introduced to the mixture through a glass column with porous glass frit at the terminal end. Air flow as increased until bubbles were visible and a small amount of foam was observed above the surface of the liquid. After 25 minutes of stirring with air sparge, a sample of the resulting solution was diluted 10000× and analyzed by ion chromatography, which indicated 96% conversion of remaining nitrite ion.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description but by the claims and any equivalents.

What is claimed is:

1. A method for preparing 5-nitrotetrazolate and its sodium salt comprising: introducing a solution comprising 5-aminotetrazolate into reactor wherein said reactor comprises sodium nitrite solution at pH between 3 and 7 and a strong acidic cation exchange resin to produce a first reaction solution comprising 5-nitrotetrazolate.

2. The method of claim 1, further comprising transferring the first reaction solution comprising 5-nitrotetrazolate from the reactor to a second reactor comprising a strong acidic cation exchange resin to form a second reaction solution comprising 5-nitrotetrazolate concentration that is greater than the 5-nitrotetrazolate in the first reaction solution.

3. The method of claim 1, wherein the pH in the reactor is maintained at between 4 and 7 by addition of acid.

4. The method of claim 3, wherein the acid is nitric acid, sulfuric acid, hydrochloric acid or perchloric acid.

5. The method of claim 1, wherein the reactor is a fixed bed reactor, tubular slurry reactor, or fluidized bed reactor.

6. The method of claim 1, wherein the reactor is a batch reactor.

7. The method of claim 1, wherein the reactor is a continuous flow reactor.

8. The method of claim 1, wherein the reactor is a continuous stir tank reactor.

9. The method of claim 1, further comprising the step of transferring the first reaction solution to a purification reactor to remove impurities.

10. The method of claim 9, wherein the pH of the purification reactor is maintained at between 0 and 4.

11. The method of claim 9, wherein the temperature of the purification reactor is 10° C. to 30° C.

12. The method of claim 9, wherein the pH of the purification reactor is kept between 0 and 4 through continuous addition of acid.

13. The method of claim 12, wherein the acid is nitric acid, sulfuric acid, hydrochloric acid or perchloric acid.

14. A method for preparing salts of 5-nitrotetrazolate comprising:

reacting a solution comprising sodium 5-aminotetrazole in a first reactor wherein said reactor comprises sodium nitrite solution at pH between 3 and 7 and a strong acidic cation exchange resin to produce a reaction solution containing 5-nitrotetrazolate; transferring said reaction solution into at least one additional reactor containing a strong acidic cation exchange resin to form a second reaction solution comprising 5-nitrotetrazolate concentration that is greater than the 5-nitrotetrazolate in the first reaction solution; and transferring the second reaction solution into a purification reactor.

15. The method of claim 14, wherein the pH of the purification reactor is maintained at between 0 and 4.

16. The method of claim 14, where the reaction solution is continuously removed from one reactor into the purification reactor.

* * * * *